(12) United States Patent
Burke et al.

(10) Patent No.: US 8,895,312 B2
(45) Date of Patent: Nov. 25, 2014

(54) NANOFLUIDIC PLATFORM FOR SINGLE MITOCHONDRIA ANALYSIS

(71) Applicant: The Regents of the University of California, Oakland, CA (US)

(72) Inventors: Peter Burke, Irvine, CA (US); Katayoun Zand, Irvine, CA (US); Ted Pham, Westminster, CA (US); Antonio Davila, Philadelphia, PA (US); Douglas Wallace, Swarthmore, PA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/963,813

(22) Filed: Aug. 9, 2013

(65) Prior Publication Data
US 2014/0051174 A1    Feb. 20, 2014

Related U.S. Application Data

(60) Provisional application No. 61/691,165, filed on Aug. 20, 2012.

(51) Int. Cl.
| | |
|---|---|
| G01N 33/58 | (2006.01) |
| G01N 21/05 | (2006.01) |
| G01N 1/18 | (2006.01) |
| B01L 3/00 | (2006.01) |
| G01N 33/50 | (2006.01) |
| G01N 15/14 | (2006.01) |

(52) U.S. Cl.
CPC ........ *G01N 33/582* (2013.01); *B01L 3/502761* (2013.01); *B01L 2300/123* (2013.01); *B01L 2200/0668* (2013.01); *B01L 2300/0861* (2013.01); *G01N 33/5005* (2013.01); *G01N 15/1484* (2013.01); *B01L 2300/0816* (2013.01)
USPC ............. 436/63; 436/164; 436/165; 436/172; 436/180; 422/82.08; 422/502; 422/505; 435/287.3; 435/288.3; 435/288.4; 435/288.7

(58) Field of Classification Search
USPC ........... 436/63, 164, 165, 172, 174, 177, 180; 422/82.05, 82.08, 501, 502, 503, 504, 422/505, 513, 534, 551; 435/4, 29, 30, 34, 435/283.1, 287.1, 287.3, 288.3, 288.4, 435/288.7
See application file for complete search history.

(56) References Cited

U.S. PATENT DOCUMENTS

| | | | |
|---|---|---|---|
| 8,131,112 B1* | 3/2012 | Gourley | 382/280 |
| 2007/0248971 A1* | 10/2007 | Maerkl et al. | 435/6 |
| 2011/0253222 A1* | 10/2011 | Arai | 137/1 |
| 2012/0247980 A1* | 10/2012 | Burke et al. | 205/792 |

OTHER PUBLICATIONS

Arakawa et al. Biomicrofluidics, vol. 5, 2011, pp. 014114-1 to 014114-11.*
Zand et al. Analytical Chemistry, vol. 85, 2013, pp. 6018-6025.*

(Continued)

*Primary Examiner* — Maureen Wallenhorst
(74) *Attorney, Agent, or Firm* — Vista IP Law Group LLP

(57) ABSTRACT

A microfluidic device for mitochondria analysis includes an inlet coupled to a first access channel, an outlet coupled to a second access channel, and a plurality of trapping channels fluidically coupled at one end to the first access channel and fluidically coupled at an opposing end to the second access channel, each trapping channel has a cross-sectional dimension about 2 μm in one direction and a cross-sectional dimension between about 0.45 and about 0.75 μm in a second direction.

17 Claims, 9 Drawing Sheets

(56) References Cited

OTHER PUBLICATIONS

Zare, R.N. & Kim, S. Microfluidic platforms for single-cell analysis. Annual review of biomedical engineering 12, 187-201 (2010).

Nagrath, S. et al. Isolation of rare circulating tumor cells in cancer patients by mi-crochip technology. Nature 450, 1235-1239 (2011).

Lecoeur, H. et al. Real-time flow cytometry analysis of permeability transition in isolated mitochondria. Experimental cell research 294, 106-17 (2004).

Medina, J.M., L6pez-Mediavilla, C. & Orfao, A. Flow cytometry of isolated mito-chondria during development and under some pathological conditions, FEBS Letters 510, 127-1 32 (2002).

Strack, A., Duffy, C.F., Malvey, M. & Arriaga, E.A. Individual mitochondrion char-acterization: A comparison of classical assays to capillary electrophoresis with laser-induced fluorescence detection. Analytical Biochemistry 294, 141-147 (2001).

Fuller, K.M., Arriaga, E.A. & A, E.A.A. Advances in the analysis of single mitochondria. Current Opinion in Biotechnology 14,35-41 (2003).

Duffy, C.F., MacCraith, B., Diamond, D., O'Kennedy, R. & Arriaga, E.A. Fast elec-trophoretic analysis of individual mitochondria using microchip capillary electrophoresis with laser induced fluorescence detection. Lab Chip 6, 1007-1011 (2006).

Johnson, R.D. et al. Analysis of mitochondria isolated from single cells. Analytical and Bioanalytical Chemistry 387, 107-118 (2007).

Kostal, V. & Arriaga, E.A. Recent advances in the analysis of biological particles by capillary electrophoresis. Electrophoresis 29, 2578-2586 (2008).

Kostal, V., Katzenmeyer, J. & Arriaga, E.A. Capillary electrophoresis in bioanalysis. Analytical Chemistry 80, 4533-4550 (2008).

Huser, J. & Blatter, L.A. Fluctuations in mitochondrial membrane potential caused by repetitive gating of the permeability transition pore. Biochemical Journal 343, 311-317 (1999).

Huser, J., Rechenmacher, C.E. & Blatter, L.A. Imaging the Permeability Pore Tran-sition in Single Mitochondria. Biophysical Journal 74, 2129-2137 (1998).

* cited by examiner

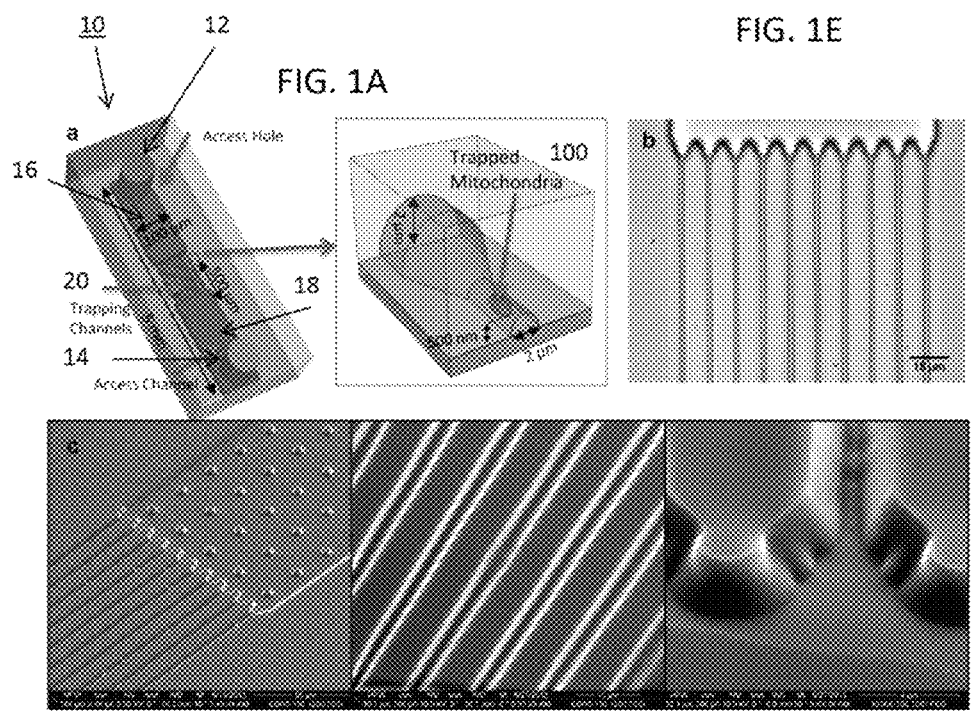

NANOFLUIDIC PLATFORM FOR SINGLE MITOCHONDRIA ANALYSIS

RELATED APPLICATION

This Application claims priority to U.S. Provisional Patent Application No. 61/691,165 filed on Aug. 20, 2012, which is hereby incorporated by reference in its entirety Priority is claimed pursuant to 35 U.S.C. §119.

STATEMENT REGARDING FEDERALLY SPONSORED RESEARCH OR DEVELOPMENT

This invention was made with Government support under Grant No. 1R21CA143351-01 awarded by the National Institute of Health Cancer Institute; Grant Nos. AG24373, NS21328, AG13154, DK73691 awarded by the National Institute of Health; and Grant No. MURI W911NF-11-1-0024 awarded by the Army Research Office. The Government has certain rights in this invention.

FIELD OF THE INVENTION

The field of the invention generally relates to microfluidic devices. More particularly, the invention pertains to microfluidic devices and methods of making the same that are used to trap cellular organelles such as mitochondria.

BACKGROUND OF THE INVENTION

The vast majority of assays performed on mitochondrial function are on large quantities of mitochondria, typically requiring $10^7$ cells worth of sample. While there exist a few techniques such as flow cytometry and capillary electrophoresis that can be used to investigate individual mitochondria, none of these are suitable for the studies and application envisioned with the technology described herein.

Several studies have demonstrated the application of flow cytometry to the analysis of individual mitochondria and provide evidence for a heterogeneous population, thus further motivating the technology development presented herein. Flow cytometry has the advantage of using existing commercially available instruments. Flow cytometry provides a "snap shot" of a single mitochondrial state (e.g. JC-1 fluorescence, forward scatter and side scatter). In this way, statistical analysis of mitochondria under various conditions and states can be obtained. The use of flow cytometry cannot be used to track the status of individual mitochondria over a longer period of time. In flow cytometry, a single mitochondria flows quickly past the detectors for a short interrogation time (less than 1 ms), never to be interrogated again.

Similar to flow cytometry, capillary electrophoresis with laser-induced fluorescence detection allows for analysis of single mitochondria. In this technique, a 50 μm capillary guides individual mitochondria which migrate in response to a high electric field (ca. 200 V/cm). Using this technique, a variety of mitochondrial properties can be assayed, such as the electrophoretic mobility, the cardiolipin content, and ROS production. As in flow cytometry, single mitochondria are analyzed at a snapshot in time as they migrate passed the detection window. Again, the technique is able to analyze large number of mitochondria and their variations. However, an extended duration analysis of a single mitochondrion is not possible. In addition, a membrane potential assay has not yet been demonstrated with this approach. Possible complications of the large electric field to the membrane potential have not yet been addressed.

An alternative technique to immobilize isolated mitochondria involves adhesion to a glass microscope slide. This technique allows visualization and characterization of up to hundreds of individual mitochondria in a single field of view. A disadvantage of this approach, however, is the large fluorescence background of the fluorophore outside of the mitochondria. If one seeks to quantitatively determine $\Delta\psi m$ using potential sensitive dyes, it is necessary to carefully measure the ratio of the dye fluorescence intensity at the inside to the outside of the mitochondria. The measurement is complicated by the large diffuse fluorescence background of the fluorophore outside of the mitochondria. In addition, parallel processing of multiple analytes is not possible on a glass slide.

SUMMARY

In one embodiment, the invention includes a microfluidic device that is configured to trap individual mitochondria in one or more submicron-sized fluidic channels. The fluidic channels may be formed in a material such as PDMS that is bonded or otherwise adhered to a substrate such as glass or the like. The microfluidic device, in on preferred embodiment, includes an inlet, an outlet, and a plurality of trapping channels interposed between the inlet and outlet. The trapping channels are dimensioned to trap individual mitochondria therein. The trapping channels at like a filter wherein individual mitochondria are trapped along the channels one-by-one but fluid can still pass.

In one embodiment, a microfluidic device for mitochondria analysis includes an inlet coupled to a first access channel; an outlet coupled to a second access channel; and a plurality of trapping channels fluidically coupled at one end to the first access channel and fluidically coupled at an opposing end to the second access channel, each trapping channel comprises a cross-sectional dimension about 2 μm in one direction and a cross-sectional dimension between about 0.45 and about 0.75 μm in a second direction.

In another embodiment, a method of analyzing mitochondria includes flowing fluorescently labeled mitochondria through a plurality of trapping channels, with each trapping channel having a cross-sectional dimension about 2 μm in one direction and a cross-sectional dimension between about 0.45 and about 0.75 μm in a second direction; trapping one or more mitochondria within the plurality of trapping channels; and imaging the trapped one or more mitochondria over a period of time.

The device may be used for the trapping and interrogation of individual, isolated mitochondria. Its application has been demonstrated in fluorescence microscopy of individual isolated mitochondria. But the application is not limited to fluorescence microscopy. It could, for instance, be used for electrical interrogation of mitochondria.

BRIEF DESCRIPTION OF THE DRAWINGS

FIG. 1A illustrates a schematic representation of one embodiment of the microfluidic device.

FIG. 1E illustrates a brightfield microscopic image of the device.

FIG. 1F illustrates three SEM images of the trapping channels formed in PDMS.

DESCRIPTION OF THE ILLUSTRATED EMBODIMENTS

Figures 1B, 1C, 1D:
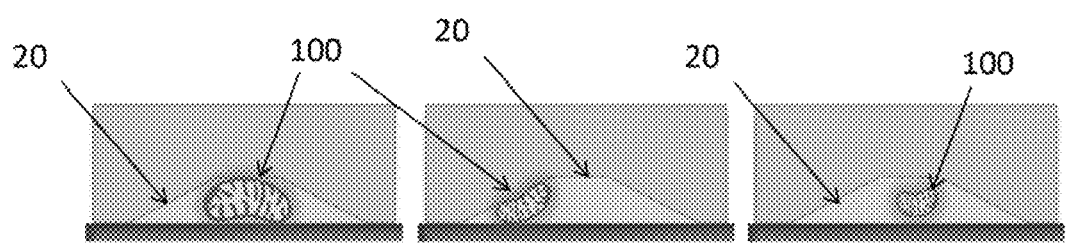
FIGS. 1B-1D illustrates cross-sectional views of a trapping channel with different sized mitochondria contained therein.

FIG. 1A illustrates a schematic representation of one embodiment of the microfluidic device 10. The device includes an inlet 12, and outlet 14, access channels 16, 18 interfacing with the inlet 12 and outlet 14, respectively, and a plurality of trapping channels 20 interposed between access channels 16, 18. The number of trapping channels 20 may vary with parallel processing requiring at least two trapping channels 20 but typically there are at least five or more. The access channels 16, 18 may have a number of dimensions. One exemplary dimension is for each access channel 16, 18 to have a width of around 100 µm and a height of around 2 µm. FIG. 1A also includes a magnified perspective view of a mitochondria 100 being trapped within a single trapping channel 20 of the array of trapping channels. The trapping channels 20 are dimensioned to trap individual mitochondria 100 therein. For example, an individual trapping channel may have a width of around 2 µm which is larger than the width of a typical mitochondria (0.2-1.2 µm). A typical morphology of mitochondria is a cigar-shape. The height of the channels (0.45-0.75 µm) is almost equal to the average diameter of a typical mitochondria. Of course, the dimensions of the width/height may be reversed. That is to say, one of the dimensions (height or width) should be close to the diameter of a mitochondria. In FIG. 1A, the trapping channel 20 has a width of 2 µm and a height of 0.5 µm. Of course, other dimensions within this approximate range may also be used.

FIGS. 1B, 1C, and 1D illustrates cross-sectional views of a trapping channel 20 with different sized mitochondria contained therein. First, the trapping channel 20 has a trapezoid cross-section. For example, the trapezoid may have a cross-section at the base of around 3.5 µm that gradually narrows at the top (as illustrated in FIGS. 1B, 1C, and 1D) to around 400 nm. The average width of the trapping channel 20 (width at the middle of the trapezoid) is around 2 µm which is larger than the diameter of mitochondria. The trapping mechanism can be seen with reference to FIGS. 1B, 1C, and 1D. In FIG. 3A, larger mitochondria get trapped at the middle of the trapping channel 20. With reference to FIG. 3B, smaller mitochondria get trapped at the corners, leaving room for other mitochondria to pass. As seen in FIG. 3C, some small mitochondria will pass through the middle of the trapping channel 20 without getting trapped. The length of the trapping channels 20 may vary but an exemplary length may be around 500 µm.

FIG. 1E illustrates a brightfield microscopic image of the device. Ten (10) trapping channels 20 are illustrated although it should be understood that fewer or more trapping channels 20 may be employed. As seen in FIG. 1E, the trapping channels 20 may be formed by a gradual tapering from the access channels 16, 18. FIG. 1F illustrates three SEM images of the trapping channels 20 formed in PDMS at different magnification levels.

The mitochondria are physically trapped along the trapping channels 20. Since the height of the trapping channels 20 at their highest point is similar to the average diameter of mitochondria but the width is around two times larger, the trapping channels 20 act like a filter where fluid can pass through but individual mitochondria are trapped along the trapping channels 20 one by one. Due to variations in size of individual mitochondria and also the trapezoidal cross section of the trapping channels 20, occasionally one sees that one mitochondrion is trapped in some location in the trapping channel 20, but a smaller mitochondrion can pass along the first mitochondrion and get trapped at a further downstream location. Exact determination of trapping locations requires mathematical simulations, but based on experimental observations it is believed that mitochondria that are already trapped at the trapping channel 20 entrance due to the small height of the trapping channel 20 behave like obstacles that disrupt the flow in the narrow trapping channel 20 and create vertical components in the flow direction (vertical to the channel direction). The flow direction, variations in mitochondria size, and the trapezoidal cross section of the trapping channel 20 result in mitochondria getting trapped at random locations along the trapping channel 20. It has been found experimentally that for a flow rate of 10 µL/h, the concentration of mitochondria in the flow buffer that results in an appropriate number of trapped mitochondria for imaging is around 50 µg/mL of mitochondrial protein. This concentration is over an order of magnitude lower than what is used in most experiments. The number of trapped mitochondria for each experiment using the described conditions is generally 20-40 in the entire field of view (or around 3-6 mitochondria within the field of view of the imaging device). It is possible to increase the throughput by increasing the number of trapping channels 20 and using an imaging system with higher resolution and larger field of view. Flow rates into the device may vary.

Figure 2:
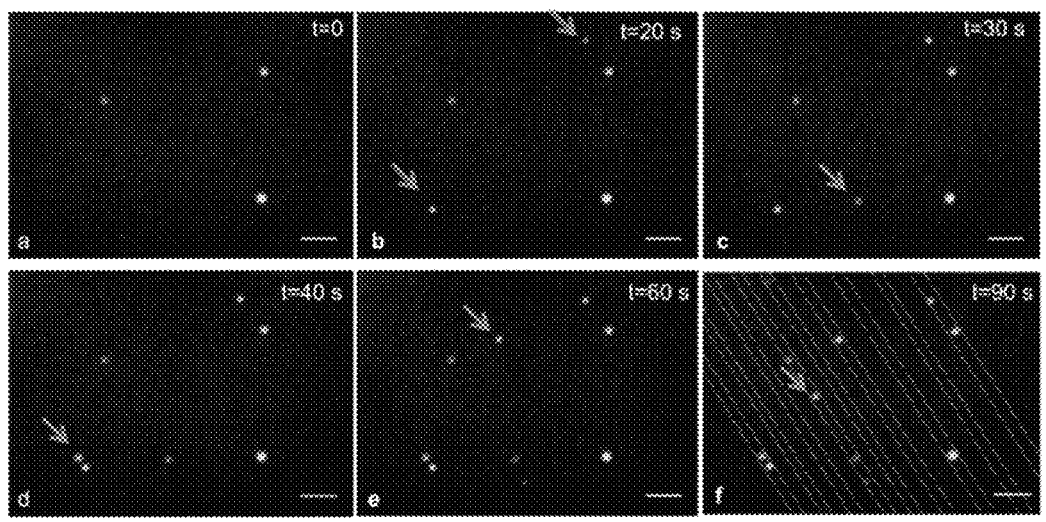
FIG. 2 illustrates a series of time images of Mito Tracker Green (MTG) labeled mitochondria trapped within the microfluidic device.

Mitochondria solution can be introduced into the trapping channels 20 with a pump such as, for example, a syringe pump. Individual mitochondria start to get trapped in the trapping channels 20, and their population gradually goes up as the flow continues. In FIG. 2, an example trapping experimental run is shown. FIG. 2 illustrates a series of time images of Mito Tracker Green (MTG) labeled mitochondria. In each image, a new mitochondrion appears that has been flowed in from the reservoir and trapped inside the trapping channel 20. Arrows indicate the addition of new mitochondria. Dashed lines in panel image (f) suggests the outline of the channels.

Brightfield and fluorescence images are captured separately and merged later. Scale bar is 10 µm. Mitochondria stained with MTG are flowed into channels with a rate of 10 µL/h. Time-lapse microscopy of the channels is performed at the same time. In all experiments where mitochondria were imaged, their position was fixed after the initial introduction. The chemical environment can be adjusted through additional fluid flow at rates of up to a few µL per minute. Thus, the mitochondria are gently trapped inside the trapping channels 20, enabling access to fluid for them, but they are not moving.

Figure 3:
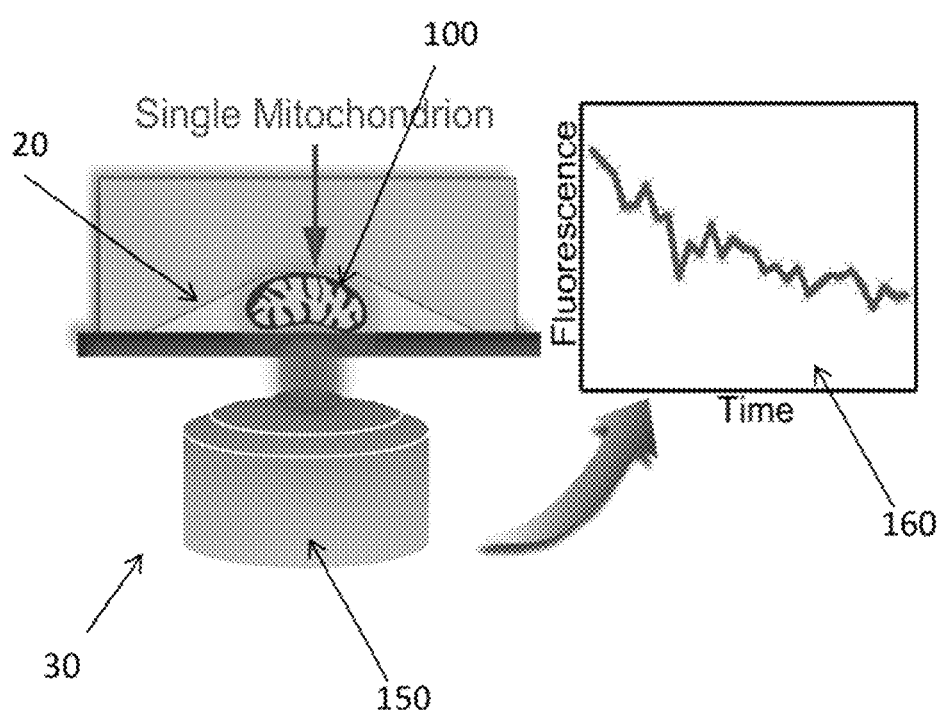
FIG. 3 illustrates a system for single mitochondrial analysis according to one embodiment.

FIG. 3 illustrates a system 30 for single mitochondrial analysis according to one embodiment. A cross-sectional view of a trapping channel 20 is illustrated with a single mitochondria 100 contained therein. An imaging device 150 is illustrated imaging the single mitochondria 100 trapped within the trapping channel 20. In this embodiment, the mitochondria 100 is labeled with the fluorescent marker. The imaging device 150 (or a separate device) is configured to illuminate the mitochondria 100 with excitation radiation. The fluorescent marker then emits fluorescent radiation which is imaged by the imaging device 150. The fluorescence of the mitochondria 100 may then be monitored as a function of time given that the mitochondria 100 is trapped within the trapping channel 20. FIG. 3 illustrates a display 160 showing the fluorescence intensity as a function of time. The mitochondria 100 may, for example, be subject to different chemical environments and interrogated via a variety of fluorescent dyes.

In experiments described herein, mitochondria 100 were imaged with an Olympus IX71 inverted fluorescence microscope, equipped with a 12 bit monochromatic CCD camera (QIClick-F-M-12), a 60X, 0.7 NA objective, 120 W mercury vapor excitation light source and standard FITC (490 nm-525 nm) and TRITC (557 nm-576 nm) filters. Image analysis was done with ImageJ software. A 3×3 median filter was used to remove noise. For fluorescence intensity measurements the area with the highest intensity at the center of each mitochondrion image was selected and the fluorescence intensity was averaged over the selected area. Background fluorescence was removed by choosing three neighbor regions with the same area selected for the mitochondria. The fluorescence intensity was averaged over the three regions and subtracted from the mitochondrial intensity. The standard deviation in the background fluorescence intensity causes some small error (less than 10% in most cases) in calculating the fluorescence intensity.

Mitochondria were isolated from the human cervical cancer cell line HeLa (ATCC, CCL-2). The adherent cells were cultured and maintained in log growth phase in media consisting of EMEM (ATCC, 30-2003) supplemented with 10% FBS (Invitrogen, 10438-018) and 1% penicillinstreptomycin (ATCC, 30-2300). All other chemicals were obtained from Sigma Aldrich, unless otherwise noted.

Mito Tracker green (MTG), obtained from Life Technologies, is a mitochondrial selective fluorescent probe that binds to mitochondria proteins regardless of the membrane potential of the mitochondria and emits a bright green fluorescence at 519 nm when excited at 490 nm. Mitotracker Green forms a dye-protein complex with free thiol groups inside the mitochondria, yielding significantly higher fluorescence than free dye in aqueous solution. It is reported that this increase could be as much as 40-fold. We used MTG to visualize the mitochondria in the channels. To stain the mitochondria, we diluted the dye in dimethyl sulfoxide (DMSO) to a concentration of 100 µM and then diluted it 1000-fold in the respiration buffer to a concentration of 100 nM.

To monitor the membrane potential of the trapped mitochondria, 5,5',6,6'-tetrachloro-1,1',3,3'-tetraethylbenzimidazolyl-carbocyanine iodide (JC-1) obtained from Sigma Aldrich was used. In energized mitochondria the membrane potential promotes an uptake of JC-1 into the mitochondrial matrix according to the Nernst equation. The high concentration of JC-1 forms aggregates inside the mitochondria. When JC-1 is excited at 488 nm, it emits with peaks at 530 nm (green) and 590 nm (red). The intensity of the red emission strongly depends on the concentration of J-aggregates and therefore on the membrane potential of the mitochondria.

Energized mitochondria emit a bright red fluorescence at 590 nm. In mitochondria with low membrane potential the dye does not form aggregates inside the mitochondria and the red fluorescence decreases. It has been shown that there is a significant correlation between the ratio of red to green fluorescence of this dye and the membrane potential of mitochondria. Ttetramethylrhodamine methyl ester (TMRM) purchased from Life Technologies was also used in some experiments. TMRM is a lipophilic cationic dye with red-orange fluorescence that is accumulated by mitochondria according to the Nernst equation. The fluorescence intensity of the stained mitochondria can be used to estimate the mitochondrial membrane potential. By monitoring the time-dependence of the fluorescence of the inner mitochondrial membrane, one can obtain qualitative information about the dynamics of the membrane potential. It was observed that TMRM sticks to the PDMS channel and produces a high background fluorescence which makes it difficult to distinguish the mitochondria from background. For JC-1 assays, JC-1 was dissolved in DMSO and then added to the mitochondria sample to a final dye concentration of 300 nM. The solution was mixed and incubated at room temperature for 7 min. TMRM was added with the same method. Various concentrations of TMRM were used ranging from 100 nM to 2 nM.

The device may be fabricated in Polydimethylsiloxane (PDMS). A mold is fabricated by photolithography of a positive photoresist on a silicon substrate (e.g., Microposit SC1827 positive photoresist on silicon wafer). The photolithography parameters are tailored to slightly overdevelop the sub-micron channels and create multiple height features with a single lithography step, so that the narrower channels also have a smaller height. The PDMS portion that contains the channels therein can be bonded to another substrate such as glass using conventional PDMS manufacturing techniques.

The following explains an exemplary fabrication process of the device using PDMS. A silicon wafer with photoresist patterns is used as the mold for soft lithography of PDMS. To fabricate the mold, a silicon wafer was cleaned with 120° C. Piranha solution (3:1 mixture of sulfuric acid and hydrogen peroxide) for 1 hour, rinsed in DI water, dried with nitrogen, and dehydrated at 200° C. The wafer was primed with hexamethyldisilazane (HMDS). Channel patterns were fabricated by photolithography of Microposit SC1827 positive photoresist. The photoresist was spin coated on the wafer at 3500 rpm for 30 s, prebaked at 90° C. for 30 min in a convection oven, and exposed to G-Line UV light through a chromium(105 nm)/glass mask using Karl Suss MA6 mask aligner with soft contact between the mask and the wafer. The dosage of exposure was set at 160 mJ/cm$^2$. Microposit MF-319 was used for developing. The developing takes around 25 s.

Soft contact is used for lithography because the contact between the mask and the resist surface is not very close, and there is a slight gap between the two surfaces (compared to vacuum contact). Due to diffraction of light passing through the mask, light that reaches the plane of the wafer does not have a step function intensity distribution; regions of the photoresist near the pattern edges get some light exposure even though they are covered by opaque parts of the mask. This is a well-known phenomenon in positive photoresist lithography that usually leads to trapezoidal cross section of the developed photoresist instead of a rectangular cross section. It can be avoided or reduced by using vacuum contact between the mask and the resist surface, lowering the dosage of exposure and using a photoresist with higher contrast. Here, we are using this phenomenon to get multiple heights with a single lithography step. Due to small width of the channel, the whole width of the channel receives some dosage of exposure; for each channel the edges get more exposure, while the light intensity decreases gradually as it gets closer to the center of the channel. The resist regions that receive a higher exposure dissolve faster in the developer. When the wafer is placed in the developer solution, the regions that are exposed through the transparent parts of the mask have the fastest dissolution rate, while the resist at the trap channel region gets dissolved at a slower rate, with the lowest rate at the center (vertical axis of symmetry); therefore, the trap channels lose some of their height. In case of the larger features (access channels), the edges get some light exposure, but the mask protects the bulk of the feature from light exposure; therefore, larger features keep their original height after the development step. This method is very reproducible, and out of the ten (10) molds that were fabricated, the multiple height patterns were obtained on seven (7) of them. Using the given lithography parameters the height of the trapping channels 20 ranged from 450 nm to 750 nm.

Silicone elastomer and curing agent (Sylgard 184, Dow Corning Co.) were mixed thoroughly at a 10:1 weight ratio. PDMS was degassed for 30 min in a vacuum desiccator and poured over the salinized mold to a thickness of 3 mm. The mold was placed in a 70° C. curing oven overnight. After curing, PDMS was easily cut and peeled off from the mold. Inlet and outlet holes were punched with a diameter of 0.63 mm to allow connection to the syringe pump. To seal the channels the chips were exposed to 70 W oxygen plasma treatment at 100 mTorr left in 70° C. oven for 20 min to complete the bonding process. The oxygen plasma treatment causes the PDMS to become hydrophilic, making it easy to introduce the aqueous solution into the channels after bonding. However, after about a day the sidewalls would become hydrophobic again, and the channels were not reusable. Fluidic channels were filled with the respiration buffer without mitochondria first, and the buffer containing mitochondria was flown into the channels later.

Figures 4A, 4B, 4C:
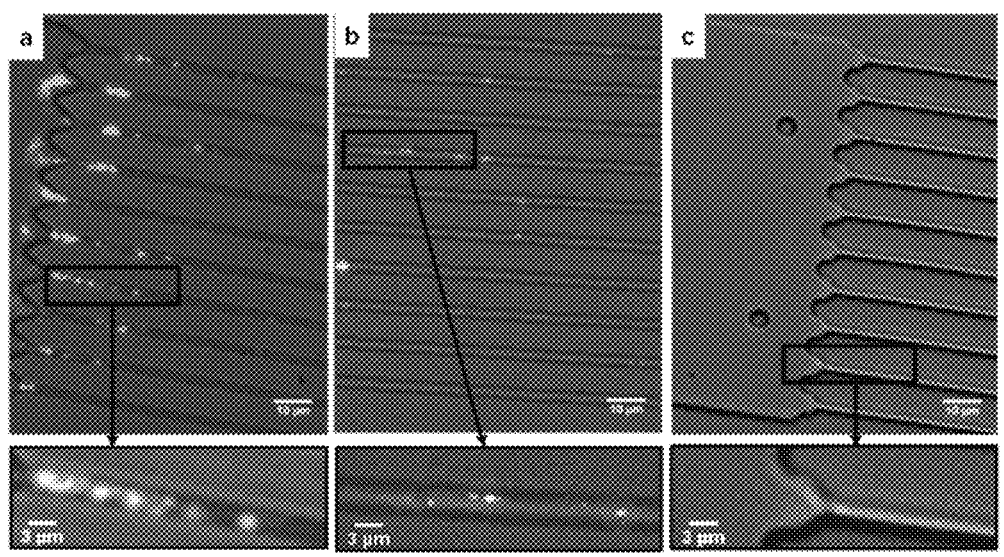
FIG. 4A, 4B, and 4C illustrate fluorescent images of fluorescently labeled mitochondria (labeled with JC-1, red fluorescence shown) at various concentrations.
Figures 5A, 5B, 5C:
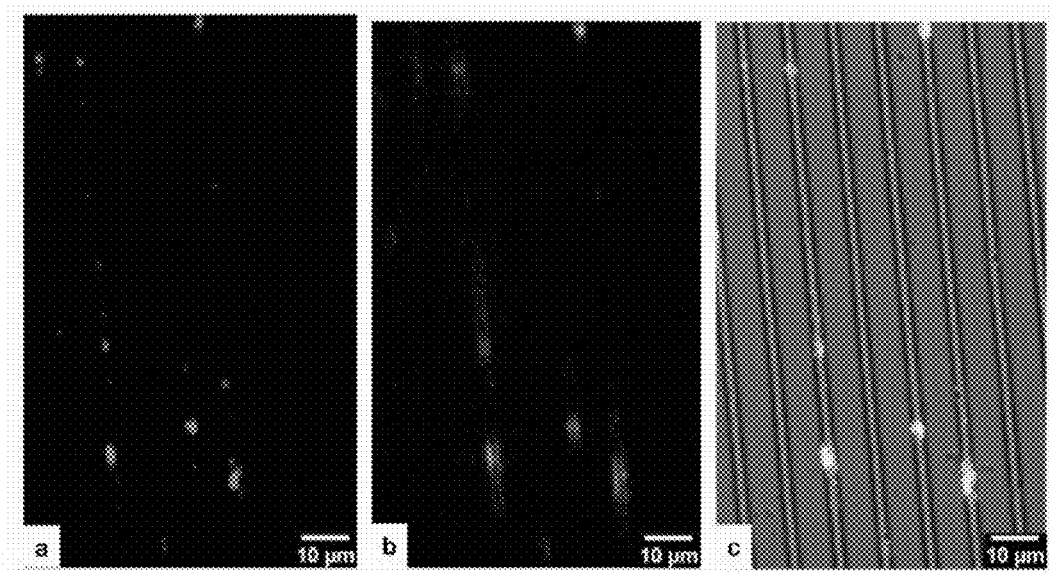
FIG. 5A illustrates a fluorescent image (taken with red filter) of trapped mitochondria stained with JC-1).
FIG. 5B illustrates a fluorescent image of the same trapped mitochondria taken with a green filter.
FIG. 5C illustrates an overlapped image of FIG. 5A, FIG. 5B, and a brightfield image of the trapping channels.

FIGS. 4A, 4B, and 4C illustrate fluorescent images of fluorescently labeled mitochondria (labeled with JC-1, red fluorescence shown). Different concentrations of trapped mitochondria are achieved by changing the mitochondria concentration in the filling solution. All channels have been pumped with the mitochondria solution at a rate of 10 μL/hour for 2 minutes. FIG. 4A illustrates 300 μg/mL protein concentration (density too high). FIG. 4B illustrates 50 μg/mL protein concentration (density optimum). FIG. 4C illustrates 1 μg/mL protein concentration (density low). FIG. 5A illustrates a fluorescent image (taken with red filter) of trapped mitochondria stained with JC-1). FIG. 5B illustrates a fluorescent image of the same trapped mitochondria taken with a green filter. FIG. 5C illustrates an overlapped image of FIG. 5A, FIG. 5B, and a brightfield image of the trapping channels. The protein concentration was 100 μg/mL.

Figure 5D:
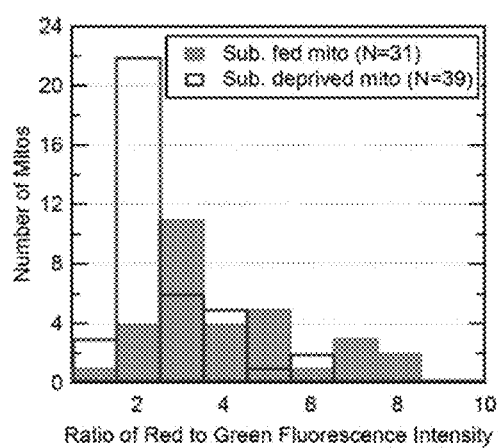
FIG. 5D is a graph of the ratio of red to green fluorescent intensity vs. number of mitochondria.

The mitochondria in the trapping channels 20 are vital and sustain a membrane potential. This can be demonstrated using the fluorescence dye JC-1. In FIGS. 5A and 5B, separate red and green fluorescence images of the same mitochondria are shown. FIG. 5C shows their superposition over the bright-field image of the nanochannels. JC-1 stained mitochondria are provided with 10 mM sodium succinate and flown into channels with a rate of 10 μL/h. After 2 min the flow is stopped and the channels are imaged. Clearly, the mitochondria are trapped individually in the trapping channels 20, and a large percentage of them are bright red (as seen in FIG. 5A), indicating the membrane potential is still large. The solid bars in FIG. 5D show the histogram of red/green fluorescence intensity for thirty one (31) mitochondria that were in the field of imaging. Around 80% of the mitochondria have a ratio of 3 or higher. As a control, the same experiment was conducted with substrate deprived mitochondria that are expected to have a lower membrane potential. The distribution of red/green fluorescence intensity ratio for the deprived mitochondria in this sample is shown by the un-filled bars in FIG. 5D. Out of thirty nine (39) mitochondria, 65% have a ratio of 2 or lower.

Figure 6A:
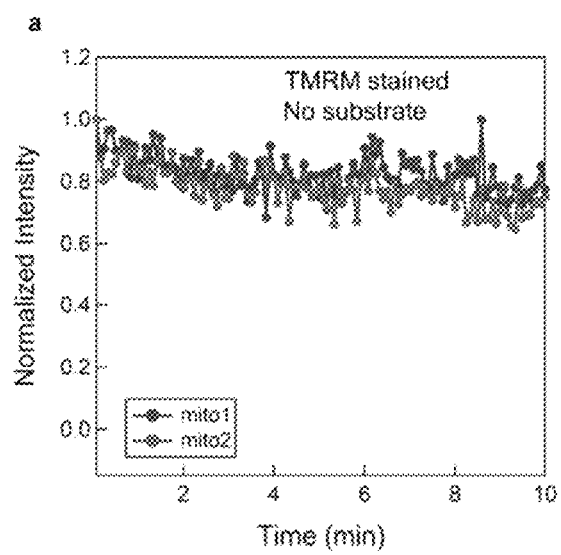
FIG. 6A illustrates normalized TMRM fluorescent intensity from two individual trapped mitochondria imaged every 5 seconds.
Figure 6B:
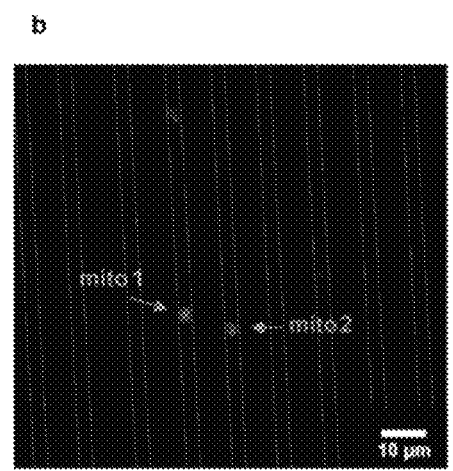
FIG. 6B illustrates the two individual trapped mitochondria from which the intensity data was obtained. Dashed lines suggest outlines of channels.

To monitor the time dependent membrane potential, time-lapse microscopy of stained trapped mitochondria was performed for over ten minutes with continuous illumination. Mitochondria stained with 30 nM TMRM were introduced into the trapping channels, and an image was captured every 5 s, with an image acquisition time of 2.5 s per image. As can be seen in FIG. 6A, the fluorescence intensity from TMRM stained mitochondria remains relatively constant indicating that the trapped mitochondria maintain their membrane potential for a long time. FIG. 6B illustrates the two individual trapped mitochondria from which the intensity data was obtained. The substrate response and MMP experiments described next were performed using JC-1. Because of the particular microscope setup used, only one filter cube at a time can be used for time-lapse fluorescence microscopy and thus cannot measure both red and green simultaneously. Because of this the red intensity was monitored which has been reported to be linearly correlated with membrane potential. To account for the inaccuracies such as those caused by the apparent size of mitochondria compared to their real size that might be caused by using the red fluorescence only, the normalized traces for each mitochondrion are shown. Each trace is divided by the fluorescence intensity measured for that mitochondrion at time zero, so that all the traces start at intensity of one. This way the data is not comparing different mitochondria. Instead, the data show the trend of membrane potential change for one mitochondrion.

Figure 7A:
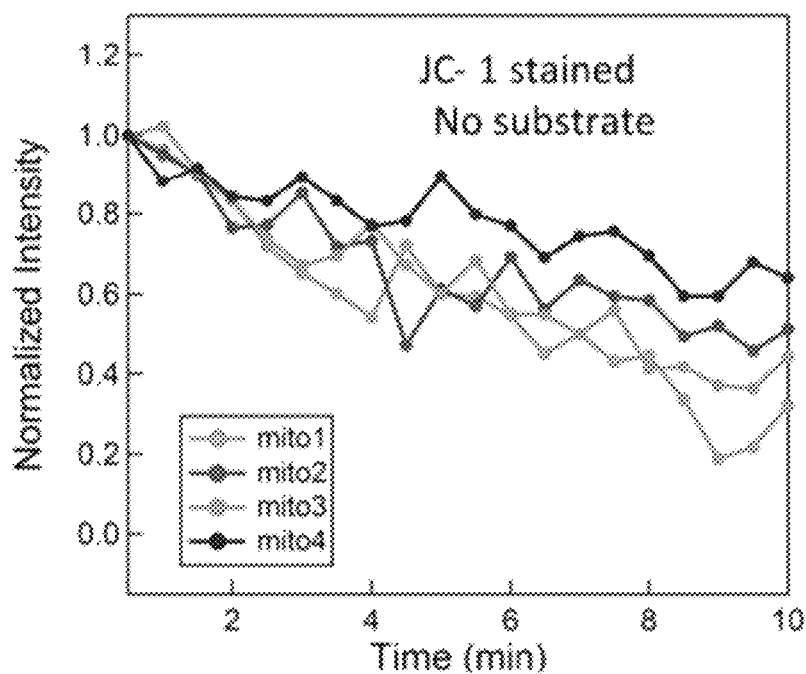
FIG. 7A normalized red fluorescence intensity of JC-1 stained mitochondria as function of time. Substrates are not used.
Figure 7B:
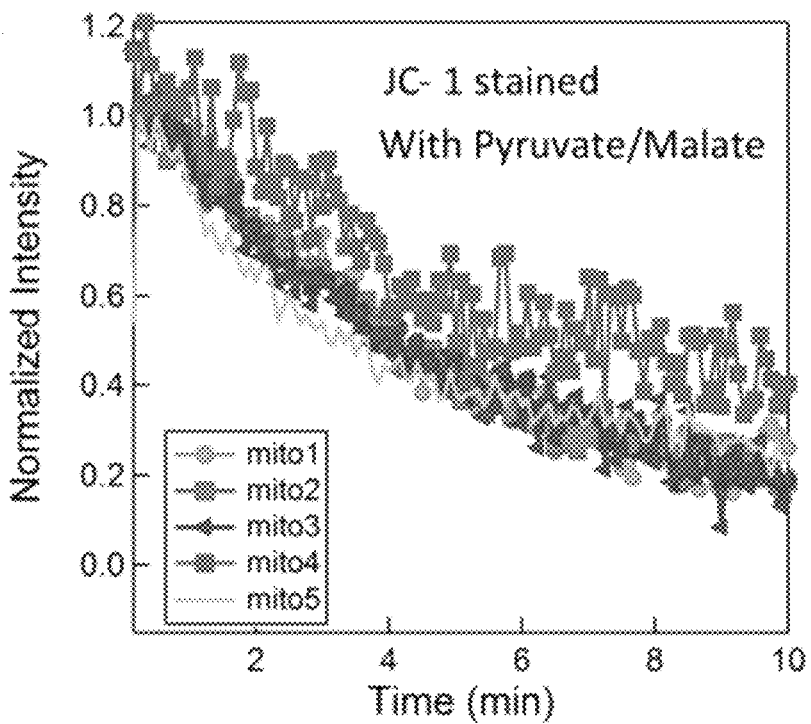
FIG. 7B illustrates normalized red fluorescence intensity of JC-1 stained mitochondria as function of time after OXPHOS substrates (5 mM pyruvate and 5 mM malate) are added to respiration buffer just before flowing the mitochondria into the trapping channel(s).

Without OXPHOS substrates, the electron transport chain is idle, and the membrane potential remains in its basal, resting state. In order to demonstrate the ability to chemically modulate the electron transport chain and the bioenergetics state of the mitochondria in the trapping channels 20, a series of experiments were performed with and without OXPHOS substrates pyruvate/malate present in the respiration buffer. In FIGS. 7A and 7B, two sets of experiments are shown in which the mitochondria are labeled and imaged with JC-1. In FIG. 7A, substrates are not used. In FIG. 7B, OXPHOS substrates, 5 mM pyruvate and 5 mM malate, are added to JC-1 stained mitochondria respiration buffer just before flowing the mitochondria in the channels. This activates the electron transport chain and initially increases the mitochondrial membrane potential $\Delta\psi m$. As mitochondria gradually consume the substrates, the substrate concentration decreases; therefore, the membrane potential and fluorescence intensity gradually drop and become identical to the sample without substrates.

Typical normalized red fluorescence intensity of JC-1 stained mitochondria is shown in FIG. 7A (each curve shows the fluorescence from a single mitochondrion.) It is observed that for JC-1 stained mitochondria the fluorescence intensity has dropped around 50% during the time span that they were continuously illuminated for photography, and this is believed to be attributed to photobleaching of the JC-1 since experiments with identical buffer but different stain (TMRM) showed no appreciable decay in the membrane potential. FIG. 7B illustrates the fluorescence intensity (normalized) measurement of JC-1 stained mitochondria (five different mitochondria) in the presence of OXPHOS substrates. The fluorescence intensity decays with time but this time with a higher rate, due to gradual consumption of OXPHOS substrates.

Interestingly, for one of the mitochondria (labeled mito4 in FIG. 7B), around 20% fluctuation in the fluorescence intensity was observed. Fluctuations (flickering) of membrane potential of individual mitochondria from different cell types have been reported before, although the detailed conditions and causes of this flickering are not fully understood.

This is the first observation of such flickering in isolated mitochondria from HeLa cell line, and it is surprising that it is observed in substrate fed (rather than basal) mitochondria, which is contradictory to some other studies, where removal of substrates resulted in flickering in some mitochondria. Even though JC-1 is a slow response dye, it has been shown that the observed flickering when using JC-1 is very similar to TMRM but with a slightly lower frequency. It is our belief that the technique demonstrated herein could be useful for future studies to more quantitatively elucidate the flickering of the membrane potential, its causes, and modulators. FIG. 7C illustrates a graph of the ratio of average absolute fluorescence intensities from a/c, after the substrates had been consumed, the membrane potential returned to its basal (idle) state.

Calcium in mitochondrial matrix controls the rate of energy production. In case of pathological calcium overload mitochondrial permeability transition pore opens irreversibly causing the mitochondria membrane to become abruptly permeable. This results in mitochondrial depolarization and swelling. A solution of 10 mM $CaCl_2$ in DI water was prepared and diluted 10 times in respiration buffer to the final calcium concentration of 1 mM. The osmolarity of the final respiration buffer solution with 1 mM $CaCl_2$ is about 310 mOsm, which is well within the physiological osmolarity range for mitochondria. A very high concentration of $Ca^{2+}$ was used to make sure that the amount of calcium that reaches the mitochondria is enough to cause the swelling. The solution was pumped into the channels (with a relatively low flow rate of 5 µL $h^{-1}$ to make sure it will not dislodge the trapped mitochondria) to induce depolarization. In order to avoid the photobleaching of JC-1, the mitochondria were imaged prior to the introduction of calcium solution, started calcium flow, stopped the light exposure, and waited for 4 min.

Figure 8:
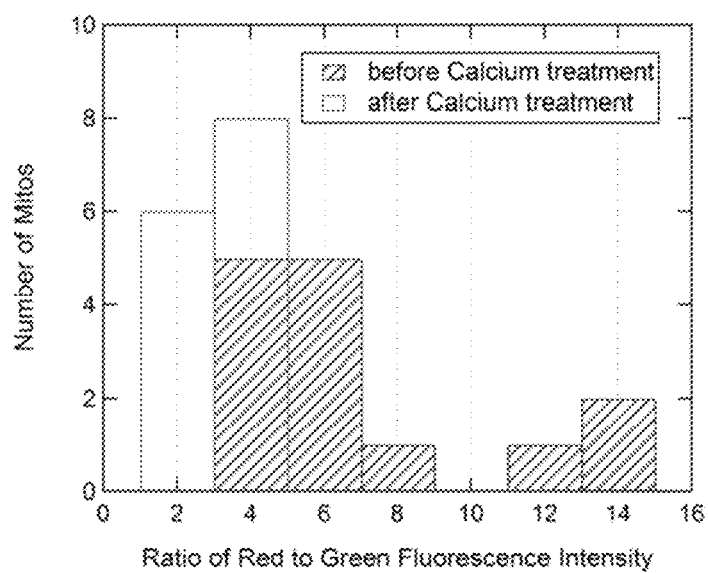
FIG. 8 illustrates a histogram showing the distribution of JC-1 fluorescence intensity ratio for the fourteen (14) mitochondria involved in the study prior to (dashed bars) and after calcium treatment (un-dashed bars).

The illumination was turned on the same field was imaged again. The red/green fluorescence intensity of most of the mitochondria had considerably decreased. This clearly indicates the membrane potential has been significantly reduced by the $Ca^{2+}$. To quantify this effect, the red fluorescence to green fluorescence intensity ratio was compared prior to and after calcium treatment. The red/green ratio for all 14 mitochondria varied but shifted to a lower value after introduction of the calcium. In FIG. 8, the histograms of the ratios (which is indicative of the membrane potential $\Delta\psi m$) for the pre- and post-calcium treatment are plotted. Interestingly, the results indicate the membrane potential has collapsed for all but one mitochondrion, regardless of the initial membrane potential (i.e., red/green ratio). This demonstrates the ability to study heterogeneity and statistical properties of individual mitochondria.

There are several advantages to the microfluidic device described herein. First, the response of individual mitochondria to a variety of chemical species can be tracked over a long period of time. In addition, as opposed to capillary electrophoresis, there is no electric field applied to the mitochondria. In the microfluidic device, the volume of solution outside of the mitochondria but held within the trapping channels is minimized. This leads to much lower levels of background fluorescence. This makes the calculation of membrane potential much easier. By having a plurality of trapping channels, the device can run parallel processing of multiple analytes using different fluid channels.

The devices and methods described herein provides a powerful stage for fluorescence imaging of isolated mitochondria in a controlled environment and real time investigation of their behavior under the influence of different chemicals. Multiple applications of the new technology can be envisioned. The application of this and similar technologies to the analysis of subcellular organelles may have a variety of applications in cancer biology, stem cell biology, drug screening, and aging studies, because of the growing consensus of the general importance of functional metabolomics in biology and medicine. For example, as one alternative embodiment, instead of fluorescent interrogation of trapped mitochondria, electrical interrogation of the trapped mitochondria may be used. Moreover, while mitochondria are principally described as being the trapped organelle, other cellular organelles may also be flowed through the device and trapped.

Multiple applications of this platform can be envisioned. These belong to a growing importance of bioenergetics and metabolism in all aspects of medicine and biology. While most work on high throughput studies of metabolism has been geared towards assays of the small molecule metabolic contents of a cell, we argue strongly that metabolomics should encompass not only the global small molecule contents, but also the energetic state and energetic fluxes (that is, the membrane potential as stored energy and the respiration rate as consumption of energy). We term this study of the energetic (rather than molecular) contents of a cell functional metabolomics. Some of the applications of this technology is discussed below.

Heteroplasmy: Heteroplasmy (differences among mitochondria even within individual cells) is a well-known but poorly quantified phenomenon. Most assays of mitochondrial suspensions measure aggregate properties. To date, prior to our work, all other assays (such as flow cytometry) measured heteroplasmy at a snapshot in time. In contrast, our work can indeed uniquely provide high throughput quantitative information about heteroplasmy as a function of time. The importance of heteroplasmy in biology has not been well established, and this is primarily because a lack of measurement tool. However, tantalizing evidence of its importance is recently being uncovered. For example, it is suspected that some autophagy pathways which degrade mitochondria do so only for low membrane potential mitochondria. Genetic defects in this pathway, which presumably depend on heteroplasmy to maintain only healthy (high membrane potential) mitochondria, are closely implicated in Parkinson's disease. In another example, mESCs with low $\Delta\Psi m$ behaved qualitatively different than those with high $\Delta\Psi m$ regarding the ease of differentiation and resistance to teratoma formation. Finally, the mitochondria within cardiomyocytes as well as differentiating stem cells shows clearly heteroplasmy of ΔΨm, having both high and low membrane potential organelles within a single cell.

Cancer biology and apoptosis: Mitochondrial membrane permeabilization can be induced by a variety of chemical signals. It is believed that once MMP has passed a critical threshold, the phenomenon self-amplifies in an all-or nothing fashion, resulting in an irreversible cascade causing apoptosis, through a variety of mechanisms. At present a variety of signals are known to induce or inhibit MMP, and thus the mitochondria acts as a decision making "gate" of sorts and the point of no return for cell death. Cancer cells are often characterized as resistant to MMP induction. Therefore, potential therapeutic actions include enhancers of MMP through proteins such as BCL-2. Whole cells are commonly used to study apoptosis and MMP. However, in isolated mitochondria one has the advantage of complete control of the surrounding media. While not the same as in vivo studies, one can control the chemical contents of the supporting buffer and thus study their effects quantitatively.

Therefore, the platform and methods described herein could allow for high-throughput, combinatorial screening of the chemical inducers and inhibitors of MMP and, thus, apoptosis, requiring small sample quantities for both the mitochondrial mass and also the candidate drugs. In addition, because of the high throughput, interference among various inhibitors and inducers can be assayed in an economical fashion.

Clinical applications: Clinical tests on mitochondrial suspensions are used to diagnose mitochondrial disease. In many of these tests a biopsy is required, and any technology that can minimize the amount of sample required would be an improvement.

Stem cell biology: A clear link between metabolism and pluripotency is suspected based on morphological evidence and other evidence of stem cell mitochondria. For example, the inner membrane of stem cell mitochondria is smooth, in contrast to that of mitochondria from virtually all other known cell lines. However, it is difficult to culture enough stem cells that are required for typical mitochondrial assays (~107 cells) while at the same time maintaining pluripotency. Therefore, platforms such as this which allow extremely small sample sizes can have important applications in investigating the relationship between mitochondrial morphology, function, metabolism, and pluripotency.

Drug toxicity screening: There is growing realization that the toxicity effects of a variety of candidate drugs act through mitochondrial related mechanisms. For this purpose, microchip based platforms using low volumes of both drug candidates and mitochondrial samples may be used to screen for drug toxicity.

While embodiments of the present invention have been shown and described, various modifications may be made without departing from the scope of the present invention. For example, dimensions illustrated in the drawings are illustrative and may vary from those specifically mentioned therein. The invention, therefore, should not be limited, except to the following claims, and their equivalents.

What is claimed is:

1. A microfluidic device for mitochondria analysis comprising:
    an inlet coupled to a first access channel;
    an outlet coupled to a second access channel; and
    a plurality of trapping channels fluidically coupled at one end to the first access channel and fluidically coupled at an opposing end to the second access channel, each trapping channel comprises a cross-sectional dimension about 2 μm in one of width or height and a cross-sectional dimension between about 0.45 and about 0.75 μm in the other of width or height.

2. The microfluidic device of claim 1, wherein the trapping channels are formed in polydimethysiloxane PDMS.

3. The microfluidic device of claim 1, further comprising a pumping source operatively coupled to the inlet.

4. The microfluidic device of claim 1, wherein the plurality of trapping channels comprises at least five channels.

5. The microfluidic device of claim 1, further comprising an imaging device configured to image the plurality of trapping channels.

6. The microfluidic device of claim 1, wherein each of the trapping channels has a trapezoidal cross-sectional shape.

7. A method of analyzing mitochondria comprising:
    flowing a sample containing mitochondria into the inlet of the device of claim 1;
    trapping at least some of the mitochondria within the trapping channels; and
    imaging the plurality of trapping channels with an imaging device, wherein the trapped mitochondria are fluorescently labeled.

8. The method of claim 7, wherein imaging comprises obtaining multiple images over a period of time and monitoring fluorescent levels as a function of time.

9. The method of claim 7, wherein in the sample containing mitochondria also contains substrates consumed by the mitochondria.

10. The method of claim 7, further comprising serially flowing different solutions through the inlet of the device.

11. The method of claim 7, wherein the sample is flowed into the device at a rate of around 10 μL/h.

12. The method of claim 7, wherein multiple mitochondria are trapped within the trapping channels.

13. The method of claim 12, wherein each trapping channel traps between about 3 and 6 mitochondria within a field of view of the imaging device.

14. A method of analyzing mitochondria comprising:
    flowing a sample containing fluorescently labeled mitochondria through a plurality of trapping channels, with each trapping channel having a cross-sectional dimension about 2 μm in one of width or height and a cross-sectional dimension between about 0.45 and about 0.75 μm in the other of width or height;
    trapping one or more mitochondria within the plurality of trapping channels; and
    imaging the trapped one or more mitochondria over a period of time.

15. The method of claim 14, wherein imaging comprises obtaining multiple images over a period of time and monitoring fluorescent levels as a function of time.

16. The method of claim 14, wherein the sample containing mitochondria also contains substrates consumed by the mitochondria.

17. The method of claim 14, further comprising serially flowing different solutions through the plurality of trapping channels.

* * * * *